United States Patent [19]

Fischli et al.

[11] Patent Number: 4,634,710
[45] Date of Patent: Jan. 6, 1987

[54] TRICYCLIC IMIDAZOLE DERIVATIVES

[75] Inventors: Albert Fischli, Riehen; Anna Krasso, Basel; Henri Ramuz, Birsfelden; André Szente, Riehen, all of Switzerland

[73] Assignee: Hoffmann-La Roche Inc., Nutley, N.J.

[21] Appl. No.: 720,775

[22] Filed: Apr. 8, 1985

[30] Foreign Application Priority Data

Apr. 19, 1984 [CH] Switzerland .................. 1966/84

[51] Int. Cl.$^4$ .................. C07D 401/12; A61K 31/415
[52] U.S. Cl. ..................................... 514/338; 546/271
[58] Field of Search .................. 546/271; 514/338

[56] References Cited

U.S. PATENT DOCUMENTS

| | | | |
|---|---|---|---|
| 3,623,882 | 11/1971 | Götze et al. | 546/271 |
| 4,248,880 | 2/1981 | Krasso et al. | 546/271 |
| 4,255,431 | 3/1981 | Junggren et al. | 546/271 |
| 4,435,406 | 3/1984 | Krasso et al. | 546/271 |
| 4,472,409 | 9/1984 | Senn-Bilfinger | 546/271 |
| 4,555,518 | 11/1985 | Rainer | 546/271 |
| 4,560,693 | 12/1985 | Rainer | 546/271 |

FOREIGN PATENT DOCUMENTS

| | | |
|---|---|---|
| 3240248 | 6/1983 | Fed. Rep. of Germany . |
| 3404610 | 2/1984 | Fed. Rep. of Germany . |
| 2134523 | 8/1984 | United Kingdom . |

Primary Examiner—Jane T. Fan
Attorney, Agent, or Firm—Jon S. Saxe; Bernard S. Leon; Matthew Boxer

[57] ABSTRACT

Tricyclic imidazole derivatives of formula I

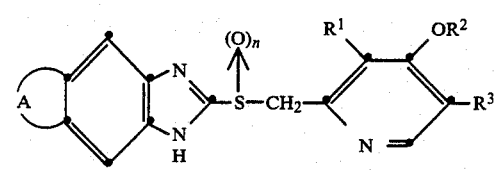

wherein one of $R^1$ and $R^3$ is lower alkyl and the other is hydrogen or lower alkyl, $R^2$ is lower alkyl, n is the number 0 or 1, A is

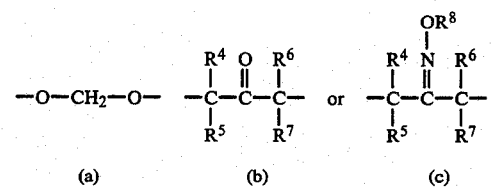

$R^4$, $R^5$, $R^6$ and $R^7$ each is lower alkyl and $R^8$ is hydrogen or lower alkyl, and their acid addition salts are described. These compounds are useful as agents for control or prevention of ulcers and of increased gastric acid secretion.

30 Claims, No Drawings

TRICYCLIC IMIDAZOLE DERIVATIVES

BRIEF DESCRIPTION OF THE INVENTION

The invention relates to imidazole derivatives of the formula

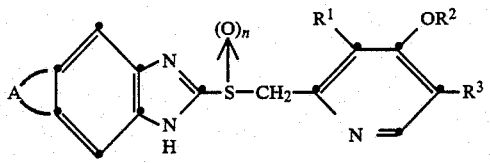

wherein one of $R^1$ and $R^3$ is lower alkyl and the other is hydrogen or lower alkyl, $R^2$ is lower alkyl, n is the number 0 or 1, A is

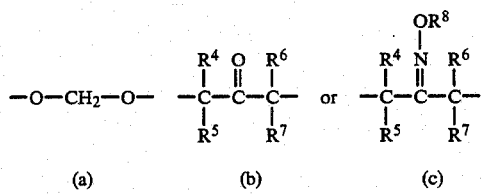

$R^4$, $R^5$, $R^6$ and $R^7$ each is lower alkyl and $R^8$ is hydrogen or lower alkyl, and their acid addition salts.

These compounds are distinguished by valuable pharmacodynamic properties, in that they inhibit the formation of ulcers and the gastric acid secretion with low toxicity.

Objects of the invention are compounds of formula I and their acid addition salts, the compounds of formula I as pharmaceutically active substances, the preparation and intermediates for the preparation of the compounds of formula I and their acid addition salts, medicaments containing a compound of formula I or an acid addition salt thereof and the preparation of such medicaments, as well as the use of the compounds of formula I and their acid addition salts in the control or prevention of illnesses, especially in the control or prevention of ulcers and of increased gastric acid secretion, or the use of the compounds of formula I and their acid addition salts for the preparation of medicaments for the control or prevention of ulcers and of increased gastric acid secretion.

DETAILED DESCRIPTION OF THE INVENTION

As used herein the term "alkyl" denotes straight-chain and branched saturated hydrocarbon residues such as methyl. ethyl, n-propyl, isopropyl, n-butyl, isobutyl and the like. The term "alkoxy" denotes alkyl ether groups wherein alkyl is as describe above. The term "lower", when used to describe organic compounds, denotes residues or compounds with at most 7, preferably at most 4, carbon atoms.

The invention relates to compounds of the formula

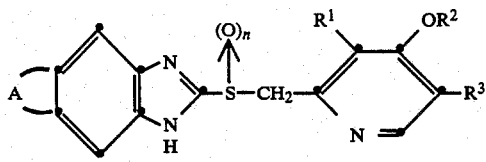

wherein one of $R^1$ and $R^3$ is lower alkyl and the other is hydrogen or lower alkyl, $R^2$ is lower alkyl, n is the number 0 or 1, A is

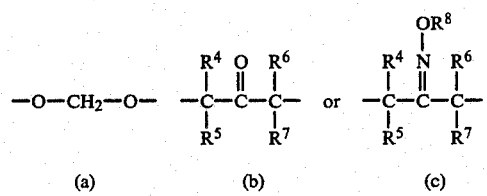

$R^4$, $R^5$, $R^6$ and $R^7$ each is lower alkyl and $R^8$ is hydrogen or lower alkyl, and their acid addition salts.

Among the compounds of formula I there are preferred those in which A is of formula (b) or (c) described above. In this case, $R^4$, $R^5$, $R^6$ and $R^7$ preferably are the same and each preferably is methyl. When the symbol A in formula I is a residue of formula (c) described above, then, moreover, $R^8$ preferably is hydrogen or methyl.

$R^2$ is preferably methyl or ethyl in formula I. With respect to the symbols $R^1$ and $R^3$ in formula I, then preferably either $R^1$ is hydrogen and $R^3$ is methyl or $R^1$ is methyl and $R^3$ is hydrogen or $R^1$ and $R^3$ each is methyl.

An especially preferred tricyclic imidazole derivative embraced by formula I described earlier is:

5,7-dihydro-2-[[(4-methoxy-3-methyl-2-pyridyl)methyl]thio]-5,5,7,7-tetramethylindeno[5,6-d]imidazol-6(1H)-one.

Further preferred compounds of formula I are:
5,7-Dihydro-2-[[(4-methoxy-3-methyl-2-pyridyl)methyl]sulfinyl]-5,5,7,7-tetramethylindeno[5,6-d]imidazol-6(1H)-one;
2-[[(4-ethoxy-3-methyl-2-pyridyl)methyl]thio]-5,7-dihydro-5,5,7,7-tetramethylindeno[5,6-d]imidazol-6(1H)-one;
2-[[(4-ethoxy-3-methyl-2-pyridyl)methyl]sulfinyl]-5,7-dihydro-5,5,7,7-tetramethylindeno[5,6-d]imidazol-6(1H)-one;
5,7-dihydro-2-[[(4-methoxy-3,5-dimethyl-2-pyridyl)methyl]thio ]-5,5,7,7-tetramethylindeno[5,6-d]imidazol-6(1H)-one;
5,7-dihydro-2-[[(4-methoxy-3,5-dimethyl-2-pyridyl)methyl]sulfinyl]-5,5,7,7-tetramethylindeno[5,6-d]imidazol-6(1H)-one;
5,7-dihydro-2-[[(4-methoxy-5-methyl-2-pyridyl)methyl]thio]-5,5,7,7-tetramethylindeno[5,6-d]imidazol-6(1H)-one;
5,7-dihydro-2-[[(4-methoxy-5-methyl-2-pyridyl)methyl]sulfinyl]-5,5,7,7-tetramethylindeno[5,6-d]imidazol-6(1H)-one;
2-[[(4-ethoxy-5-methyl-2-pyridyl)methyl]thio]-5,7-dihydro-5,5,7,7-tetramethylindeno[5,6-d]imidazol-6(1H-one;
2-[[(4-ethoxy-5-methyl-2-pyridyl)methyl]sulfinyl]-5,7-dihydro-5,5,7,7-tetramethylindeno[5,6-d]imidazol-6(1H)-one;
5,7-dihydro-2-[[(4-methoxy-3-methyl-2-pyridyl)methyl]thio]-5,5,7,7-tetramethylindeno[5,6-d]imidazol-6(1H)-one O-methyl oxime; and
5,7-dihydro-2-[[(4-methoxy-3-methyl-2-pyridyl)methyl]sulfinyl]-5,5,7,7-tetramethylindeno[5,6-d]imidazol-6(1H)-one O-methyl oxime.

Compounds of formula I in which A is of formula (a) described above include:

6-[[(4-Methoxy-3-methyl-2-pyridyl)methyl]thio]-5H-1,3-dioxolo[4,5-f]benzimidazole;
6-[[(4-methoxy-3-methyl-2-pyridyl)methyl]sulfinyl]-5H-1,3-dioxolo[4,5-f]benzimidazole;
6-[[(4-methoxy-3,5-dimethyl-2-pyridyl)methyl]thio]-5H-1,3-dioxolo[4,5-f]benzimidazole; and
6-[[(4-methoxy-3,5-dimethyl-2-pyridyl)methyl]sulfinyl]-5H-1,3-dioxolo[4,5-f]benzimidazole.

The compounds of formula I and their acid addition salts can be prepared in accordance with the invention by (a) reacting a compound of the formula

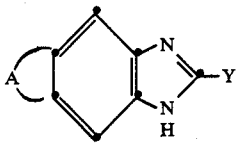  II wherein A is as described above and Y is as described below, with a compound of the formula

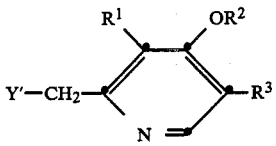  III wherein $R^1$, $R^2$ and $R^3$ are as described above and Y' is as described below, whereby one of Y and Y' is a mercapto group and the other is a leaving group; or (b) oxidizing a compound of formula I described above in which n is 0 to give a corresponding compound in which n is 1; or (c) reacting a compound of formula I described above in which A is of formula (b) described above and n is 0 with a compound of the formula $H_2N-OR^8$  IV wherein $R^8$ is as described above; or (d) treating a compound of the formula

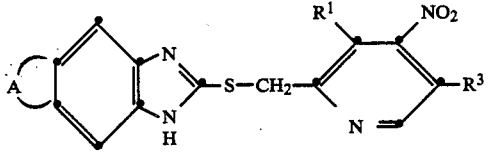  V wherein $R^1$, $R^3$ and A are as described above, with an agent yielding a lower alkoxy group; or (e) reacting a compound of the formula

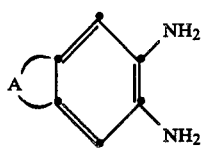  VI wherein A is as described above, with a compound of the formula

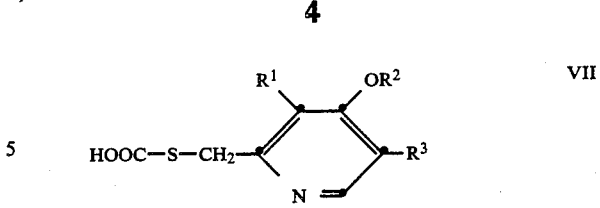  VII wherein $R^1$, $R^2$ and $R^3$ are as described above; or (f) reacting a compound of the formula

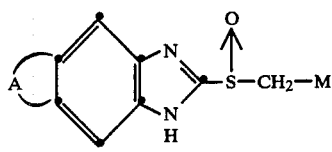  VIII wherein A' is of formula (a), (b) or (c) as described above, with the proviso that in formula (c) $R^8$ is lower alkyl, and M is an alkali metal atom, with a compound of the formula

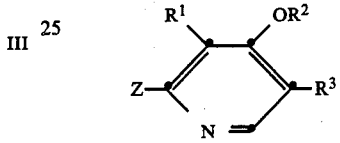  IX wherein $R^1$, $R^2$ and $R^3$ are as described above, and Z is a leaving group; and, if desired, converting a free base obtained into an acid addition salt and/or converting an acid addition salt obtained into the free base or into another acid addition salt.

In a particular embodiment of the process in accordance with the invention, compounds of formula I in which A is of formula (a) as described above are prepared in accordance with process variant 8d), (e) or (f).

According to process aspect (a) in accordance with the invention, a compound of formula II is reacted with a compound of formula III, whereby either the symbol Y in formula II is a mercapto group and the symbol Y' in formula III is a leaving group or the symbol Y in formula II is a leaving group and the symbol Y' in formula III is a mercapto group. Leaving groups are, for example, halogen atoms, especially chlorine, bromine or iodine, or suitable acid residues, especially residues of strong organic sulfonic acids. e.g. arylsulfonyloxy residues such as tosyloxy, or alkylsulfonyloxy residues such as mesyloxy. Alkylsulfinyl residues such as methylsulfinyl are further examples of leaving groups. The reaction of the compounds of formulae II and III is conveniently carried out in the presence of a solvent or solvent mixture which is inert under the reaction conditions and optionally in the presence of a base. As bases there are suitable for this purpose especially inorganic bases such as sodium or potassium hydroxide, sodium or potassium carbonate and the like or organic bases such as triethylamine or other tertiary amines. As solvents or solvent mixtures there are suitable primarily alcohols such as ethanol, mixtures of alcohols and water, acetone, ethers such as tetrahydrofuran, halogenated hydrocarbons such as methylene chloride or chloroform, dimethylformamide etc. The reaction temperature is variable in fairly wide limits and it conveniently lies between about room temperature and about the boiling point of the reaction mixture.

According to process aspect (b) in accordance with the invention, a compound of formula I in which n is the number 0 is oxidized to give a corresponding compound in which n is the number 1. Thereby, a sulfur atom is converted into the sulfinyl group and there are accordingly used for this purpose oxidation agents which are customary for such conversions, for example peracids such as m-chloroperbenzoic acid, hydrogen peroxide, peresters, sodium metaperiodate, and the like. The oxidation is conveniently carried out in an organic solvent which is inert under the reaction conditions, for example in a halogenated hydrocarbon such as methylene chloride, chloroform, dichloroethane and the like or in a hydrocarbon such as benzene and the like; when hydrogen peroxide is used as the oxidation agent it can also be carried out in acetic acid, aqueous acetic acid and the like. It is advantageous to use the oxidation agent in a slight excess with respect to the compound to be oxidized. The oxidation is conveniently carried out at room temperature or below, preferably at temperatures of about $-50°$ to about $0°$ C.

According to process aspect (c) in accordance with the invention, compounds of formula I in which A is of formula (b) and n is the number 0 are reacted with a compound of formula IV. The compound of formula IV is conveniently used in the form of an acid addition salt, for example as the hydrochloride. The reaction is conveniently carried out in a solvent which is inert under the reaction conditions, for example in an alcohol such as methanol, ethanol and the like or in mixtures thereof with water. It can be advantageous to carry out the reaction in the presence of an acid-binding agent such as potassium or sodium carbonate and the like. The reaction temperature is not critical; it can conveniently lie between about room temperature and the boiling point of the reaction mixture.

According to process aspect (d) in accordance with the invention, a compound of formula V is treated with an agent yielding a lower alkoxy group. This is conveniently carried out by heating the compound of formula V for a fairly long time, e.g. for about 4–24 hours, in a solution of the agent yielding a lower alkoxy group which can be an alkali metal lower alkoxide in the corresponding lower alkanol, for example, in methanolic sodium methylate or in ethanolic sodium ethylate. The addition of an inorganic base such as sodium carbonate and the like can be advantageous. The reaction is conveniently carried out at a temperature between about $40°$ C. and the boiling point of the reaction mixture.

According to process aspect (e) in accordance with the invention, a compound of formula VI is reacted with a compound of formula VII. This reaction is conveniently carried out in a polar solvent, which optionally contains water, in the presence of a strong acid such as hydrochloric acid and the like. Furthermore, the reaction is conveniently carried out at about the boiling point of the solvent or solvent mixture which is used.

According to process aspect (f) in accordance with the invention, a compound of formula VIII is reacted with a compound of formula IX. The alkali metal atom denoted by the symbol M in formula VIII is conveniently a lithium, sodium or potassium atom. As leaving groups (Z in formula IX) there are suitable, for example, reactive halogen atoms, especially chlorine atoms, or hydroxyl groups activated by esterification, e.g. arylsulfonyloxy residues such as tosyloxy or alkylsulfonyloxy residues such as mesyloxy. The reaction is conveniently carried out in an inert solvent, for example in an aromatic hydrocarbon such as benzene or toluene. The reaction temperature usually lies between about $0°$ C. and about $120°$ C., with the boiling point of the solvent used being preferred.

Depending on the process conditions and the starting materials used the compounds of formula I are obtained either as free bases or as acid addition salts. The free bases can be converted into corresponding acid addition salts by reaction with organic or inorganic acids, with the use of those acids which form therapeutically compatible salts, for example hydrogen chloride, hydrogen bromide, phosphoric acid, sulfuric acid, citric acid, p-toluenesulfonic acid and the like, being preferred. The acid addition salts of the compounds of formula I can be converted in a manner known per se into the corresponding free bases or into other acid addition salts. The acid addition salts of compounds of formula I in which n is the number 1 have a low stability in aqueous solution.

The starting materials of formula V are a part of the invention. Their preparation can be carried out in analogy to process aspect (a) in accordance with the invention by reacting a compound of formula II with a compound of the formula

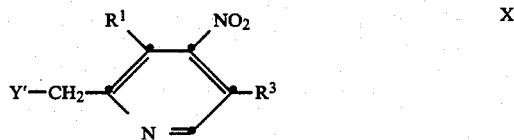

wherein $R^1$, $R^3$ and $Y'$ are as described above.

The starting materials of formulae II–IV and VI–X are known or can be prepared readily according to methods which are known per se and which are familiar to any person skilled in the art; moreover, some of the Examples hereinafter contain detailed information concerning the preparation of certain compounds of formulae II, III and X in which Y or Y' is chlorine and of formula III in which Y' is a mercapto group.

As mentioned earlier, the tricyclic imidazole derivatives of formula I and their acid addition salts are compounds with valuable pharmacodynamic properties.

Compounds of formula I were investigated with respect to their anti-ulcer activity, to their gastric acid secretion-inhibiting activity as well as to their toxicity.

The experimental procedure described hereinafter was used to determine the anti-ulcer activity:

Groups each comprising 8 male rats with a body weight of 130–150 g are used for each dosage of a test substance. Before the beginning of the experiment the animals receive no food for 24 hours, but receive water ad libitum. Various dosages of the substances to be tested (suspended in 0.5% tragacanth) or the vehicle alone (controls) are administered twice orally, namely 1 hour before and 2 hours after the oral administration of 20 mg/kg of indomethacin. In the control animals this dosage of indomethacin leads to lesions of the stomach within 5 hours. The animals are sacrificed 6 hours after the first administration of the substance under investigation (or of the vehicle alone). The rats which remain protected from the occurrence of macroscopically visible lesions to the mucous membrane of the stomach are counted. The $ED_{50}$ is that dosage of a test substance at which 50% of the animals are protected from the occurence of such lesions.

The experimental procedure described hereinafter was used to determine the gastric acid secretion-inhibiting activity:

A part of the stomach fundus of female and male beagle hounds is separated from the remainder of the stomach in the form a pouch of the Heidenhain type (modification of the method described by Rudick et al. in J. Surgical Research 7, 383-398 (1967)). In the pouch there is fitted a steel cannula which is conducted externally through the abdominal wall. Before each experiment the animals receive no food for 18 hours, but receive water ad libitum. They are conscious and standing during the experiment and their gastric acid secretion is stimulated by the intraveous infusion of 4-methylhistamine, a selective agonist of the histamine $H_2$-receptors. The gastric acid production is determined in 15 minute fractions of the stomach pouch juice. As soon as the gastric acid production has a constant value, the substances to be tested are administered orally as a dry powder filled into gelatine capsules. The $ED_{50}$ is that dosage of a test substance which brings about a 50% inhibition of the gastric acid production caused by 4-methylhistamine in the treated animals in comparison to the controls.

In the following Table there are given for a series of compounds of formula I the results of the testing with respect to their anti-ulcer activity and to their gastric secretion-inhibiting activity. Moreover, this Table contains data concerning the acute toxicity ($LD_{50}$ in the case of single oral administration to mice).

| Compound | Anti-ulcer ED 50 mg/kg p.o. | Gastric acid secretion-inhibition ED 50, mg/kg p.o. | Toxicity LD 50 mg/kg p.o. |
| --- | --- | --- | --- |
| A | 2 | 4.88 | >5000 |
| B | 2.3 | 5.44 | >5000 |
| C | 1.2 | 2.56 | >5000 |
| D | 1.3 | 3.59 | >5000 |
| E | 4 | 1.79 | >5000 |
| F | 6 | 1.4 | >5000 |
| G | 1.6 | 6.5 | >5000 |
| H | 5 | 7.78 | 1250-2500 |
| I | 4 | 2.25 | 1250-2500 |

A: 5,7-Dihydro-2-[[(4-methoxy-3,5-dimethyl-2-pyridyl)-methyl]thio]-5,5,7,7-tetramethylindeno[5,6-d]imidazol-6(1H)—one
B: 5,7-Dihydro-2-[[(4-methoxy-3,5-dimethyl-2-pyridyl)-methyl]sulfinyl]-5,5,7,7-tetramethylindeno[5,6-d]imidazol-6(1H)—one
C: 5,7-Dihydro-2-[[(4-methoxy-3-methyl-2-pyridyl)methyl]thio]-5,5,7,7-tetra-5,6-d]imidazol-6(1H)—one
D: 5,7-Dihydro-2-[[(4-methoxy-3-methyl-2-pyridyl)methyl]sulfinyl]-5,5,7,7-tetramethylindeno[5,6-d]imidazol-6(1H)—one
E: 6-[[(4-Methoxy-3-methyl-2-pyridyl)methyl]sulfinyl]-5H—1,3-dioxolo[4,5-f]benzimidazole
F: 6-[[(4-Methoxy-3,5-dimethyl-2-pyridyl)methyl]sulfinyl]-5H—1,3-dioxolo[4,5-f]benzimidazole
G: 2-[[(4-Methoxy-3-methyl-2-pyridyl)methyl]thio]-5,7-dihydro-5,5,7,7-tetramethylindeno[5,6-d]imidazol-6(1H)—one
H: 5,7-Dihydro-2-[[(4-methoxy-3-methyl-2-pyridyl)methyl]sulfinyl]-5,5,7,7-tetramethylindeno[5,6-d]imidazol-6(1H)—one O—methyl oxime
I: 5,7-Dihydro-2-[[(4-methoxy-3-methyl-2-pyridyl)methyl]thio]-5,5,7,7-tetramethylindeno[5,6-d]imidazol-6(1H)—one O—methyl oxime.

The compounds of formula I and acid addition salts thereof can be used as medicaments, e.g. in the form of pharmaceutical preparations. Oral administration in the form of solid pharmaceutical preparations such as tablets, coated tablets, dragees, hard gelatine capsules and soft gelatine capsules primarily is preferred. Where n is the number 1 in formula I these pharmaceutical preparations must be resistant to gastric juice. Other means of administration are; oral administration in the form of liquid pharmaceutical preparations such as solutions, emulsions and suspensions, rectal administration, e.g. in the form of suppositories, or parenteral administration, e.g. in the form of injection solutions.

As mentioned earlier, medicaments containing a compound of formula I or an acid addition salt thereof likewise form a part of the invention, as well as processes for the preparation of such medicaments, which processes comprise bringing one or more compounds of formula I or acid addition salts thereof and, if desired, one or more other therapeutically active substances into a galenical administration form together with one or more therapeutically inert excipients.

For the preparation of tablets, coated tablets, dragees and hard gelatine capsules the compounds of formula I or acid addition salts thereof can be processed with pharmaceutically inert inorganic or organic excipients. As such excipients there can be used e.g. for tablets, dragees and hard gelatine capsules lactose, maize starch or derivatives thereof, talc, stearic acid or its salts etc. For the making of pharmaceutical preparations which are resistant to gastric juice it is necessary to apply a gastric juice-resistant coating which can consist e.g. of hydroxypropylmethylcellulose phthalate.

For soft gelatine capsules there are suitable as excipients e.g. vegetable oils, waxes, fats, semi-solid and liquid polyols etc.

For the preparation of solutions and syrups there are suitable as excipients e.g. water, polyols, saccharose, invert sugar, glucose and the like.

For suppositories there are suitable as excipients e.g. natural or hardened oils, waxes, fats, semi-liquid or liquid polyols and the like.

For injection solutions there are suitable as excipients e.g. water, alcohols, polyols, glycerine, vegetable oils etc.

The pharmaceutical preparations can contain, in addition, preserving agents, solubilizers, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

In accordance with the invention the compounds of formula I and acid addition salts thereof can be used in the control or prevention of illnesses, for example in the control or prevention of ulcers and of increased gastric acid secretion. The dosage can vary within wide limits and, of course, will be fitted to the individual requirements in each particular case. In general, in the case of oral administration a daily dosage can be about 30–400 mg and in the case of intravenous administration a daily dosage can be of about 1–50 mg.

As mentioned earlier, the use of the compounds of formula I and their acid addition salts for the preparation of medicaments for the control or prevention of ulcers and of increased gastric acid secretion also form a part of the invention.

In the following Examples, which illustrate the invention but which are not intended to limit its extent in any manner, all temperatures are given in degrees Celsius.

EXAMPLE 1

(a) A solution of 24 g of 2,3-dimethylpyridine in 100 ml of methylene chloride was treated while cooling with ice with a solution of 46.6 g of m-chloroperbenzoic acid in 100 ml of methylene chloride. The reaction mixture was heated under reflux for 2 hours and concentrated in a rotary evaporator. The residue was chromatographed on silica gel with ethyl acetate/methylene chloride (3:1) as the elution agent, the medium pressure flash chromatography method being used and the pressure being produced with nitrogen gas. By recrystallization from ether there was obtained 2,3-dimethylpyridine 1-oxide of melting point 56°.

(b) A solution of 15 g of 2,3-dimethylpyridine 1-oxide in 75 ml of chloroform was boiled at reflux and treated as rapidly as possible with 37 ml of trichloroacetyl chloride (the acid chloride was added through the reflux condenser). The reaction mixture was heated under reflux for 2.5 hours, subsequently poured into a mixture of ice and sodium bicarbonate and the resulting solution was washed several times with methylene chloride. The organic phase was dried with sodium sulfate, filtered and concentrated. The residue was chromatographed on silica gel with methylene chloride, the medium pressure flash chromatography method being used and the pressure being produced with nitrogen gas. The 2-chloromethyl-3-methylpyridine obtained was processed directly.

(c) A solution of 24 g of 2-chloromethyl-3-methylpyridine in 200 ml of methylene chloride was treated while cooling with ice with a solution of 44 g of m-chloroperbenzoic acid in 200 ml of methylene chloride. The reaction mixture was heated under reflux for 2 hours and concentrated in a rotary evaporator. The residue was chromatographed on silica gel with ethyl acetate/methylene chloride (3:1) as the elution agent, the medium pressure flash chromatography method being used and the pressure being produced with nitrogen gas. The 2-chloromethyl-3-methyl-pyridine 1-oxide obtained was processed directly.

(d) 300 ml of concentrated sulfuric acid was added slowly while cooling with dry ice to 230 ml of concentrated nitric acid (68%:d=1.41), while the temperature of the mixture was not allowed to exceed 5°. A solution of 38.7 g of 2-chloromethyl-3-methylpyridine 1-oxide was added thereto and the mixture was stirred at 80° for 2 hours. The reaction mixture was poured into a mixture of ice and methylene chloride, the aqueous phase was washed several times with methylene chloride and the methylene chloride solution was extracted with 10% sodium bicarbonate solution. The organic phase was dried with sodium sulfate and concentrated. The residue is recrystallized from ethyl acetate, there being obtained 2-chloromethyl-3-methyl-4-nitropyridine 1-oxide. The product has a melting point of 126°-129°.

(e) A solution of 4.5 g of 2-chloromethyl-3-methyl-4-nitropyridine 1-oxide in 25 ml of methylene chloride and 25 ml of acetonitrile was treated with 5 ml of phosphorus trichloride and the mixture was stirred at room temperature for 20 minutes. The reaction mixture was poured on to a mixture of ice and 20 g of sodium carbonate and the resulting aqueous solution was washed several times with methylene chloride. The organic phase was dried and evaporated. The thus-obtained 2-chloromethyl-3-methyl-4-nitropyridine was processed directly.

(f) A solution of 11.5 g of 2-chloromethyl-3-methyl-4-nitropyridine and 16 g of 5,7-dihydro-2-mercapto-5,5,7,7-tetramethylindeno[5,6-d]imidazol-6(1H)-one in 200 ml of absolute acetone was treated with 13 g of finely ground potassium carbonate and the mixture was stirred at room temperature under argon for 18 hours. 100 ml of acetone were distilled off in vacuo, whereupon the residue was poured on to ice. The product which crystallized out was filtered off and dissolved in methylene chloride; the solution obtained was washed with water, dried and concentrated. By recrystallization from ethyl acetate/ether there was obtained 5,7-dihydro-5,5,7,7-tetramethyl-2-[[(3-methyl-4-nitro-2-pyridyl)methyl]thio]indeno[5,6-d]imidazol-6(1H)-one of melting point 181°-183° (decomposition).

(g) A solution of 4.4 g of 5,7-dihydro-5,5,7,7-tetramethyl-2-[[(3-methyl-4-nitro-2-pyridyl)methyl]thio]indeno[5,6-d]imidazol-6(1H)-one in 100 ml of absolute methanol was treated with 3 g of sodium methylate, whereupon the mixture was boiled at reflux for 18 hours under argon. After concentrating the reaction mixture in vacuo the residue was treated with methylene chloride, whereupon the mixture was buffered by means of glacial acetic acid; the methylene chloride phase was extracted several times with a sodium bicarbonate solution, dried and evaporated. By recrystallisation from ethyl acetate there was obtained 5,7-dihydro-2-[[(4-methoxy-3-methyl-2-pyridyl)methyl]thio]5,5,7,7-tetramethylindeno[5,6-d]imidazol-6(1H)-one of melting point 222°-226°.

EXAMPLE 2

A solution of 6 g of 5,7-dihydro-2-[[(4-methoxy-3-methyl-2-pyridyl)methyl]thio]-5,5,7,7-tetramethylindeno[5,6-d]imidazol-6(1H)-one in 90 ml of abs. methylene chloride was treated under argon at −40° to −50° within 10 minutes with a solution of 3.3 g of m-chloroperbenzoic acid in 50 ml of absolute methylene chloride. The solution was subsequently stirred for an additional 20 minutes, extracted with a 10% sodium carbonate solution, dried and evaporated with the continuous replacement of methylene chloride by ethyl acetate. There thereby crystallized 5,7-dihydro-2-[[(4-methoxy-3-methyl-2-pyridyl)-methyl]sulfinyl]-5,5,7,7-tetramethylindeno[5,6-d]imidazol-6(1H)-one which melts at 192°-194° with decomposition.

EXAMPLE 3

A mixture of 10.5 g of sodium ethylate, 20 g of sodium carbonate and 400 ml of ethanol was stirred at 50° under argon for 30 minutes and then treated with 7 g of 5,7-dihydro-5,5,7,7-tetramethyl-2-[[(3-methyl-4-nitro-2-pyridyl)methyl]thio]indeno[5,6-d]imidazol-6(1H)-one. After stirring at 50° for 5 hours under argon the reaction mixture was concentrated in vacuo. The residue was treated with methylene chloride and buffered by means of glacial acetic acid; the methylene chloride solution was extracted with sodium bicarbonate solution, dried and concentrated. The residue was chromatographed on silica gel while eluting with methylene chloride/ethyl acetate (3:1), the medium pressure flash chromatography method being used and the pressure being produced with nitrogen gas. There was obtained 2-[[(4-ethoxy-3-methyl-2-pyridyl)methyl]thio]5,7-dihydro-5,5,7,7-tetramethylindeno[5,6-d]imidazol-6(1H)-one which melts at 175°-176° after recrystallization from ether.

EXAMPLE 4

A solution of 2 g of 2-[[(4-ethoxy-3-methyl-2-pyridyl)methyl]thio]-5,7-dihydro-5,5,7,7-tetramethylindeno[5,6-d]imidazol-6(1H)-one in 35 ml of absolute methylene chloride was treated at −40° to −50° under argon within 10 minutes with 1.1 g of m-chloroperbenzoic acid in 10 ml of absolute methylene chloride. The solution was subsequently stirred for an additional 20 minutes, extracted with 10% sodium carbonate solution, dried and concentrated with the continuous replacement of methylene chloride by ethyl acetate. There thereby crystallized 2-[[(4-ethoxy-3-methyl-2-pyridyl)methyl]sulfinyl]-5,7-dihydro-5,5,7,7-tetramethyl indeno[5,6-d]imidazol-6(1H)-one which melts at 180° with decomposition.

EXAMPLE 5

A solution of 560 mg of potassium hydroxide in 1.4 ml of methanol and a solution of 700 mg of hydroxylamine hydrochloride in 3.6 ml of methanol were mixed together at 40°, whereupon the mixture was stirred for 30 minutes and 300 mg of 5,7-dihydro-2[[(4-methoxy-3-methyl-2-pyridyl)methyl]thio]-5,5,7,7-tetramethylindeno[5,6-d]imidazol-6(1H)-one were added thereto. The reaction mixture was stirred at 40° under argon for 3 days and then concentrated and treated with methylene chloride/water. The methylene chloride solution was separated, dried, filtered and evaporated. The residue was chromatographed twice on silica gel with methylene chloride/methanol (9:1), the medium pressure flash chromatography method being used and the pressure being produced with nitrogen gas. 5,7-Dihydro-2-[[(4-methoxy-3-methyl-2-pyridyl)methyl]thio]-5,5,7,7-tetramethyl indeno[5,6-d]imidazol-6(1H)-one oxime was obtained. After recrystallization from ethyl acetate the product melts at 160° with decomposition.

EXAMPLE 6

A solution of 41 mg of 5,7-dihydro-2-[[(4-methoxy-3-methyl-2-pyridyl)methyl]thio]-5,5,7,7-tetramethylindeno[5,6-d]imidazol-6(1H)-one oxime in 2 ml of absolute methylene chloride was treated at −40° to −50° under argon within 10 minutes with 22.5 mg of m-chloroperbenzoic acid in 1 ml of absolute methylene chloride. The solution was stirred for an additional 15 minutes and then extracted with 10% sodium carbonate solution, dried and concentrated with the continuous replacement of methylene chloride by ethyl acetate. There thereby crystallized 5,7-dihydro-2-[[(4-methoxy-3-methyl-2-pyridyl)methyl]sulfinyl]-5,5,7,7-tetramethylindeno[5,6-d]imidazol-6(1H)-one oxime which melts at 215°–217°.

EXAMPLE 7

A solution of 6.5 g of 5,7-dihydro-2-[[(4-methoxy-3-methyl-2-pyridyl)methyl]thio]-5,5,7,7-tetramethylindeno[5,6-d]imidazol-6(1H)-one in 50 ml of absolute methanol was treated with 6 g of O-methylhydroxylamine hydrochloride. The reaction mixture was boiled at reflux for 60 hours under argon and then concentrated and extracted with methylene chloride/sodium carbonate solution. The methylene chloride solution was separated, filtered, dried and evaporated. The residue was chromatographed on silica gel with a solution of anhydrous ammonia in ether, the medium pressure flash chromatography method being used and the pressure being produced with nitrogen gas. There was obtained 5,7-dihydro-3-[[(4-methoxy-3-methyl-2-pyridyl)methyl]thio]-5,5,7,7-tetramethylindeno[5,6-d]imidazol-6(1H)-one O-methyl oxime, which has a melting point of 100° after recrystallization from n-hexane/ether.

EXAMPLE 8

A solution of 540 mg of 5,7-dihydro-3-[[(4-methoxy-3-methyl-2-pyridyl)methyl]thio-5,5,7,7-tetramethylindeno[5,6-d]imidazol-6(1H)-one O-methyl oxime in 15 ml of absolute methylene chloride was treated at −40° to −50° under argon within 10 minutes with 290 mg of m-chloroperbenzoic acid in 5 ml of absolute methylene chloride. The solution was stirred for an additional 20 minutes and then extracted with 10% sodium carbonate solution, dried and concentrated. The residue, crystallized from ether, gave 5,7-dihydro-2-[[(4-methoxy-3-methyl-2-pyridyl)methyl]sulfinyl]-5,5,7,7-tetramethylindeno[5,6-d]imidazol-6(1H)-one O-methyl oxime of melting point 140° (decomposition).

EXAMPLE 9

(a) A solution of 183 mg of 2,3-dimethylpyridine 1-oxide in 0.6 ml of concentrated sulfuric acid was treated while cooling with ice with 0.2 ml of 65% nitric acid (d=1.4). The reaction mixture was stirred at 90° for 24 hours and poured on to a mixture of ice and sodium carbonate, whereupon the resulting mixture was extracted with methylene chloride and the methylene chloride phase was dried and evaporated. The residue, crystallized from ethanol/n-pentane, gave 2,3-dimethyl-4-nitropyridine 1-oxide of melting point 99°–102°.

(b) A solution of 2.5 g of 2,3-dimethyl-4-nitropyridine 1-oxide in 50 ml of absolute methanol was treated with 0.883 g of sodium methylate, whereupon the mixture was stirred at room temperature under argon for 2 days. The reaction mixture was concentrated and the residue was extracted with methylene chloride and saturated sodium chloride solution. The methylene chloride phase was dried and evaporated. The residue, crystallized from methylene chloride/ether, gave 4-methoxy-2,3-dimethylpyridine 1-oxide of melting point 80°–83°.

(c) A solution of 500 mg of 4-methoxy-2,3-dimethylpyridine 1-oxide in 20 ml of 1,2-dichloroethane was boiled at reflux and treated with 8.3 g of trichloroacetyl chloride. After 35 minutes the reaction mixture was poured on to ice, 10% sodium carbonate solution was added, the mixture was extracted with methylene chloride and the methylene chloride solution was dried and concentrated. The thus-obtained 2-chloromethyl-3-methyl-4-methoxypyridine was processed directly.

(d) A solution of 690 mg of 2-chloromethyl-3-methyl-4-methoxypyridine and 400 mg of 5,7-dihydro-2-mercapto-5,5,7,7-tetramethylindeno[5,6-d]imidazol-6(1H)-one in 40 ml of absolute acetone was treated with 1.9 g of finely ground potassium carbonate, whereupon the mixture was stirred at room temperature under argon for 18 hours. After concentrating the mixture in vacuo the residue was chromatographed on silica gel with methylene chloride/ethyl acetate (10:1) as the elution agent, the medium pressure flash chromatography method being used and the pressure being produced with nitrogen gas. By recrystallization from ethyl acetate/ether there was obtained 5,7-dihydro-2-[[(4-methoxy-3-methyl-2-pyridyl)methyl]thio]-5,5,7,7-tetramethylindeno[5,6-d]imidazol-6(1H)-one of melting point 218°–220°.

EXAMPLE 10

(a) To 500 ml of a 5% solution of methyl lithium in ether were added dropwise at room temperature under argon 1200 ml of ether, subsequently 35.6 g of 3,5-lutidine (3,5-dimethylpyridine) and finally 400 ml of toluene. The ether was distilled off completely, whereupon the solution was stirred at 100° for 4 hours. Ice was then added portionwise thereto while cooling with methanol/ice until the evolution of heat no longer occurred. The toluene phase was separated from the precipitated solid and was extracted with 66 ml of semiconcentrated hydrochloric acid. The separated aqueous phase was adjusted to a pH of about 10 with 3N sodium hydroxide solution while cooling and extracted twice with 300 ml of ether. The ether extracts were dried over sodium sulfate and evaporated. The residue was distilled in vacuo at 20 mm/72°–74°; there was obtained 2,3,5-collidine (2,3,5-trimethylpyridine) which had a 99.15% purity in accordance with gas chromatography.

(b) 420 ml of 30% hydrogen peroxide were added dropwise at room temperature to 246.4 g of 2,3,5-collidine and 2400 ml of glacial acetic acid. The solution was stirred at 80° overnight. The reaction mixture was then cooled to 40°, a further 420 ml of 30% hydrogen peroxide were added thereto and the mixture was heated to 80° for a further 24 hours. After evaporation in vacuo the residue was dissolved in 300 ml of water, whereupon the solution was made basic with concentrated sodium hydroxide solution while cooling, saturated with sodium chloride and extracted three times with 1 l of methylene chloride. The organic phases were dried over sodium sulfate and evaporated in vacuo. The residue was crystallized from ether/petroleum ether; there was obtained 2,3,5-trimethyl-pyridine 1-oxide of melting point 42°–44°.

(c) 65 ml of fuming nitric acid (d=1.5) were added dropwise while cooling to 210 ml of concentrated sulfuric acid. 96.5 g of 2,3,5-trimethylpyridine 1-oxide were subsequently added portionwise at 0°–5°, whereupon the mixture was stirred at room temperature for 1 hour, then heated to 90° within 3 hours and left at this temperature overnight. After cooling the solution was poured on to 1.5 kg of ice, whereupon the mixture was adjusted to pH 3 with concentrated sodium hydroxide solution and extracted three times with 500 ml of methylene chloride. The combined organic phases were washed with 1 l of water, dried over sodium sulfate and evaporated in vacuo. The residue was crystallized from ether/petroleum ether and there was obtained 2,3,5-trimethyl-4-nitropyridine 1-oxide of melting point 76°–78°.

(d) 22.6 g of sodium were dissolved in 4 l of methanol under argon. 120 g of 2,3,5-trimethyl-4-nitropyridine 1-oxide were then added portionwise thereto and the solution was left to boil under reflux overnight. The pH was adjusted to 7 by means of 5N hydrogen chloride in ethyl acetate while cooling and the mixture was then evaporated in vacuo. The residue was taken up in 1.5 l of methylene chloride, the solution was filtered through silica gel, which was rinsed with 0.5 l of methylene chloride, the combined filtrates were evaporated in vacuo and the residue was crystallized from petroleum ether. There was obtained 4-methoxy-2,3,5-trimethylpyridine 1-oxide of melting point 48°–50°.

(e) 215 ml of acetic anhydride were added dropwise at room temperature to a solution of 81.5 g of 4-methoxy-2,3,5-trimethylpyridine 1-oxide in 290 ml of chloroform. After boiling under reflux for 4 hours the solution was evaporated, the residue was dissolved in 200 ml of toluene and again evaporated. The residue was taken up in 500 ml of ethyl acetate and extracted three times with 250 ml of saturated sodium bicarbonate solution. The organic phase was dried over sodium sulfate and evaporated in vacuo. The product which remains behind as the residue was chromatographed on 400 g of silica gel with ether. There was obtained (4-methoxy-3,5-dimethyl-2-pyridyl)methyl acetate in the form of an oil.

(f) 94.9 g of (4-methoxy-3,5-dimethyl-2-pyridyl)-methyl acetate were dissolved in 570 ml of ethanol. 285 ml of 3N sodium hydroxide solution were then added dropwise thereto at 0° and the mixture was stirred at room temperature for 3 hours. The ethanol was subsequently removed in vacuo, whereupon the residual aqueous solution was extracted three times with 300 ml of methylene chloride. The organic extracts were dried over sodium sulfate and evaporated in vacuo. The residue was crystallized from petroleum ether and there was obtained 4-methoxy-3,5-dimethyl-2-pyridylmethanol of melting point 49°–51°.

(g) 75.8 g of 4-methoxy-3,5-dimethyl-2-pyridylmethanol, dissolved in 200 ml of methylene chloride, were added dropwise at 0° to 38 ml of thionyl chloride in 400 ml of methylene chloride. After stirring at room temperature for 16 hours 1800 ml of ether were added dropwise thereto while cooling and the mixture was stirred at room temperature for a further 2 hours. The precipitated crystals were filtered off under suction and washed with ether. There was obtained 2-(chloromethyl)-4-methoxy-3,5-dimethylpyridine hydrochloride of melting point 130°–131°.

(h) 18.0 g of 5,7-dihydro-2-mercapto-5,5,7,7-tetramethylindeno[5,6-d]imidazol-6(1H)-one were suspended in 400 ml of ethanol and treated while cooling with ice with 15.6 g of 2-chloromethyl-4-methoxy-3,5-dimethylpyridine hydrochloride. Thereafter, a solution of 5.6 g of sodium hydroxide in 150 ml of water was added dropwise thereto, the mixture was left to boil at reflux overnight and subsequently evaporated to dryness in vacuo. The residue was dissolved in 1000 ml of methylene chloride; the solution was washed firstly with 500 ml of 1.5N sodium hydroxide solution and then with 3×500 ml of water, dried over sodium sulfate and evaporated in vacuo. The product was purified on 300 g of silica gel with ethyl acetate/methylene chloride (1:1) as the elution agent. Crystallization from methylene chloride/petroleum ether gave 5,7-dihydro-2-[[(4-methoxy-3,5-dimethyl-2-pyridyl)-methyl]thio]-5,5,7,7-tetramethylindeno[5,6-d]imidazol-6(1H)-one of melting point 166°–168°.

(i) 2.6 g of 5,7-dihydro-2-[[(4-methoxy-3,5-dimethyl-2-pyridyl)methyl]thio]-5,5,7,7-tetramethylindeno[5,6-d]imidazol-6(1H)-one were dissolved in 50 ml of hot methanol and the solution was boiling under reflux for 10 minutes with 50 ml of a 4N solution of hydrogen chloride in methanol. After concentration in vacuo the residue was crystallized from ether and there was obtained 5,7-dihydro-2-[[(4-methoxy-3,5-dimethyl-2-pyridyl)methyl]thio]-5,5,7,7-tetramethylindeno[5,6-d]imidazol-6(1H)-one dihydrochloride of melting point 165°–170°.

EXAMPLE 11

8.3 g of 5,7-dihydro-2-[[(4-methoxy-3,5-dimethyl-2-pyridyl)methyl]thio]-5,5,7,7-tetramethylindeno[5,6-d]imidazol-6(1H)-one were dissolved in 1000 ml of methylene chloride and the solution was cooled to −10° with an ice/methanol bath. 4.3 g of m-chloroperbenzoic acid, recrystallized from methylene chloride/petroleum ether, were then introduced within 25 minutes. The solution was stirred at −10° for a further 45 minutes and then poured into a mixture of 100 ml of 2N sodium carbonate solution and ice. The aqueous phase was extracted twice with 300 ml of methylene chloride. The combined organic phases were washed neutral three times with 200 ml of water, dried over sodium sulfate and concentrated at 35° in vacuo to a volume of 150 ml. Upon the addition of petroleum ether there crystallized 5,7-dihydro-2-[[(4-methoxy-3,5-dimethyl-2-pyridyl)methyl]sulfinyl]-5,5,7,7-tetramethylindeno[5,6-d]imidazol-6(1H)-one of melting point 192°-194°.

EXAMPLE 12

5 g of 5,7-dihydro-2-[[(4-methoxy-3,5-dimethyl-2-pyridyl)methyl]thio]-5,5,7,7-tetramethylindeno[5,6-d]imidazol-6(1H)-one and 40 g of hydroxylamine hydrochloride were dissolved in 250 ml of methanol and the solution was boiled at reflux overnight under argon. After evaporation of about 200 ml of methanol in vacuo the thus-obtained suspension was poured on to ice in a separating funnel which had previously been gassed with argon. The mixture was made neutral with saturated sodium bicarbonate solution and extracted five times with chloroform/methanol (3:1). The organic extracts were dried over sodium sulfate and evaporated in vacuo. The pale rose residue was dissolved in about 1 l of ethyl acetate and the solution was filtered through 30 g of silica gel (prepared in ethyl acetate). Upon concentrating the eluate in vacuo there crystallized out 5,7-dihydro-2-[[(4-methoxy-3,5-dimethyl-2-pyridyl)methyl]thio]-5,5,7,7-tetramethylindeno[5,6-d]imidazol-6(1H)-one oxime; m.p. 233°-235°.

EXAMPLE 13

1 g of 5,7-dihydro-2-[[(4-methoxy-3,5-dimethyl-2-pyridyl)methyl]thio]-5,5,7,7-tetramethylindeno[5,6-d]imidazol-6(1H)-one oxime was dissolved in 50 ml of methylene chloride and 5 ml of methanol and the solution was cooled to −20°. 0.6 g of m-chloroperbenzoic acid, recrystallized from methylene chloride/petroleum ether, was then introduced within 5 minutes. The solution was stirred at this temperature for a further 30 minutes and then poured into a mixture of 20 ml of 2N sodium carbonate solution and ice. The aqueous phase was extracted twice with 100 ml of methylene chloride. The combined organic phases were washed neutral three times with 50 ml of water, dried over sodium sulfate and concentrated at 35° in vacuo to a volume of 25 ml. Upon the addition of petroleum ether there was brought about crystallization of 5,7-dihydro-2-[[(4-methoxy-3,5-dimethyl-2-pyridyl)methyl]sulfinyl]-5,5,7,7-tetramethylindeno[5,6-d]imidazol-6(1H)-one oxime; m.p. 215°-217°.

EXAMPLE 14

5 g of 5,7-dihydro-2-[[(4-methoxy-3,5-dimethyl-2-pyridyl)methyl]thio]-5,5,7,7-tetramethylindeno[5,6-d]imidazol-6(1H)-one and 40 g of O-methylhydroxylamine hydrochloride in 250 ml of methanol were boiled at reflux for 16 hours under argon. After removing the solvent in vacuo the residue was partitioned between methylene chloride and water and the aqueous phase was extracted three times with methylene chloride. The combined organic extracts were made neutral with saturated sodium bicarbonate solution in the presence of ice and under argon gasification. After repeated extraction with methylene chloride the organic phases were dried over sodium sulfate and evaporated in vacuo. A red impurity was removed by chromatography on silica gel with ethyl acetate. The separation of the reaction product from starting material was carried out on silica gel using toluene/methyl isobutyl ketone/pyridine (80:18:2) as the elution agent. The purity of the fractions was assayed by thin-layer chromatography using the system ethyl acetate/methyl isobutyl ketone/pyridine (80:18:2). By crystallization from acetone/water there was obtained 5,7-dihydro-2-[[(4-methoxy-3,5-dimethyl-2-pyridyl)methyl]thio]-5,5,7,7-tetramethylindeno[5,6-d]imidazol-6(1H)-one O-methyl oxime of melting point 110°-112°.

EXAMPLE 15

2.6 g of 5,7-dihydro-2-[[(4-methoxy-3,5-dimethyl-2-pyridyl)methyl]thio]-5,5,7,7-tetramethylindeno[5,6-d]imidazol-6(1H)-one O-methyl oxime were dissolved in 250 ml of methylene chloride and the solution was cooled to −30° with a dry ice/acetone bath. 1.26 g of m-chloroperbenzoic acid, recrystallized from methylene chloride/petroleum ether, were then introduced within 10 minutes. The solution was stirred at this temperature for a further 50 minutes, then poured into a mixture of 50 ml of 2N sodium carbonate solution and ice and the aqueous phase was extracted twice with 150 ml of methylene chloride. The combined organic phases were washed neutral three times with 100 ml of water, dried over sodium sulfate and concentrated in vacuo at 35° to a volume of 50 ml. Upon the addition of petroleum ether there was brought about crystallization of 5,7-dihydro-2-[[(4-methoxy-3,5-dimethyl-2-pyridyl)methyl]sulfinyl]-5,5,7,7-tetramethylindeno[5,6-d]imidazol-6(1H)-one O-methyl oxime of melting point 173°-175°.

EXAMPLE 16

(a) 4.2 g of sodium were dissolved in 780 ml of ethanol under argon. 22.3 g of 2,3,5-trimethyl-4-nitropyridine 1-oxide were then added portionwise thereto and the solution was left to boil under reflux overnight. The pH was adjusted to 7 by means of 5N hydrogen chloride in ethyl acetate while cooling and the mixture was then evaporated in vacuo. The residue was taken up in 0.5 l of methylene chloride, the solution was filtered through silica gel, which was rinsed with 200 ml of methylene chloride, the combined filtrates were evaporated in vacuo and the residue was crystallized from petroleum ether. There was obtained 4-ethoxy-2,3,5-trimethylpyridine 1-oxide of melting point 59°-61°.

(b) 75 ml of acetic anhydride were added dropwise at room temperature to a solution of 31.3 g of 4-ethoxy-2,3,5-trimethylpyridine 1-oxide in 100 ml of chloroform. After boiling under reflux for 16 hours the solution was evaporated, the residue was dissolved in 100 ml of toluene and again evaporated. The residue was taken up in 250 ml of ethyl acetate, whereupon it was extracted three times with 100 ml of saturated sodium bicarbonate solution. The organic phase was dried over sodium sulfate and evaporated in vacuo. The product was chromatographed on 170 g of silica gel with ether. There was obtained (4-ethoxy-3,5-dimethyl-2-pyridyl)methyl acetate in the form of an oil.

(c) 32.9 g of (4-ethoxy-3,5-dimethyl-2-pyridyl)methyl acetate were dissolved in 190 ml of ethanol. 95 ml of 3N sodium hydroxide solution were then added dropwise thereto at 0° and the mixture was stirred at room temperature for a further 3 hours. The ethanol was subsequently removed in vacuo and the residual aqueous solution was extracted three times with 200 ml of methylene chloride. The organic extracts were dried over sodium sulfate and evaporated in vacuo. The residue crystallized from petroleum ether and there was obtained 4-ethoxy-3,5-dimethyl-2-pyridylmethanol of melting point 58°-59°.

(d) 21.0 g of 4-ethoxy-3,5-dimethyl-2-pyridylmethanol, dissolved in 110 ml of methylene chloride, were added dropwise at 0° to 10 ml of thionyl chloride in 220 ml of methylene chloride. After stirring at room temperature for 16 hours 890 ml of ether were added dropwise thereto while cooling and the mixture was stirred at room temperature for a further 2 hours. The separated crystals were filtered off under suction and washed with ether. There was obtained 2-chloromethyl-4-ethoxy-3,5-dimethylpyridine hydrochloride of melting point 156°-158°.

(e) 7.8 g of 5,7-dihydro-2-mercapto-5,5,7,7-tetramethylindeno[5,6-d]imidazol-6(1H)-one were suspended in 200 ml of alcohol and treated while cooling with ice with 7.1 g of 2-chloromethyl-4-ethoxy-3,5-dimethylpyridine hydrochloride. Thereafter, a solution of 2.4 g of sodium hydroxide in 100 ml of water was added dropwise thereto, the mixture was left to boil at reflux overnight and subsequently evaporated to dryness in vacuo. The residue was dissolved in 500 ml of methylene chloride. The solution was washed firstly with 250 ml of 1.5N sodium hydroxide solution and then with 3×250 ml of water, dried over sodium sulfate and evaporated in vacuo. The product was purified on 150 g of silica gel with ethyl acetate/methylene chloride (1:1) as the elution agent. Crystallization from methylene chloride/petroleum ether gave 5,7-dihydro-2-[[(4-ethoxy-3,5-dimethyl-2-pyridyl)methyl]thio]-5,5,7,7-tetramethylindeno[5,6-d]imidazol-6(1H)-one of melting point 179°-180°.

EXAMPLE 17

7.3 g of 5,7-dihydro-2-[[(4-ethoxy-3,5-dimethyl-2-pyridyl)methyl]thio]-5,5,7,7-tetramethylindeno[5,6-d]imidazol-6(1H)-one were dissolved in 750 ml of methylene chloride and the solution was cooled to −10° with an ice/methanol bath. 3.7 g of m-chloroperbenzoic acid, recrystallized from methylene chloride/petroleum ether, were then introduced within 30 minutes. The solution was stirred at this temperature for a further 75 minutes and then poured into a mixture of 100 ml of 2N sodium carbonate solution and ice. The aqueous phase was extracted twice with 300 ml of methylene chloride. The combined organic phases were washed neutral three times with 200 ml of water, dried over sodium sulfate and concentrated at 35° in vacuo to a volume of 120 ml. Upon the addition of petroleum ether there was brought about crystallization of 5,7-dihydro-2-[[(4-ethoxy-3,5-dimethyl-2-pyridyl)methyl]sulfinyl]-5,5,7,7-tetramethylindeno[5,6-d]imidazol-6(1H)-one; m.p. 185°-187°.

EXAMPLE 18

(a) 400 ml of 30% hydrogen peroxide were added dropwise at room temperature to 321.5 g of 2,5-lutidine(2,5-dimethylpyridine) in 1800 ml of glacial acetic acid. The solution was stirred at 80° overnight, then cooled to 40°, treated once more with 400 ml of 30% hydrogen peroxide and heated to 80° for a further 24 hours. After evaporation in vacuo the residue was dissolved in 300 ml of water. The solution was made basic with concentrated sodium hydroxide solution while cooling, saturated with sodium chloride and extracted three times with 1 l of methylene chloride. The organic extracts were dried over sodium sulfate and evaporated in vacuo. There was obtained 2,5-dimethylpyridine 1-oxide in the form of an oil.

(b) 260 ml of fuming nitric acid (d=1.5) were added dropwise to 840 ml of concentrated sulphuric acid while cooling. 348.2 g of 2,5-dimethylpyridine 1-oxide were subsequently added portionwise at 0°-5°. The mixture was stirred at room temperature for 1 hour, then heated to 90° within 3 hours, left at this temperature overnight and, after cooling, poured on to 6 kg of ice. The mixture was adjusted to pH 3 with concentrated sodium hydroxide solution and extracted three times with 2 l of methylene chloride. The combined organic phases were washed with 4 l of water, dried over sodium sulfate and evaporated in vacuo. The residue was crystallized from methylene chloride/petroleum ether and there was obtained 2,5-dimethyl-4-nitropyridine 1-oxide of melting point 142°-144°.

(c) 12.2 g of sodium were dissolved in 2 l of methanol under argon, whereupon 60 g of 2,5-dimethyl-4-nitropyridine 1-oxide were added portionwise and the solution was left to boil under reflux overnight. The pH was adjusted to 7 with 5N hydrogen chloride in ethyl acetate while cooling and the mixture was evaporated in vacuo. The residue was taken up in 1 l of methylene chloride, the solution was filtered through silica gel, which was rinsed with 0.4 l of methylene chloride, and the combined filtrates were evaporated in vacuo. The residue crystallized from methylene chloride/petroleum ether and there was obtained 4-methoxy-2,5-dimethylpyridine 1-oxide of melting point 99°-101°.

(d) 55 ml of acetic anhydride were added dropwise at room temperature to a solution of 19.9 g of 4-methoxy-2,5-dimethylpyridine 1-oxide in 75 ml of chloroform. After boiling under reflux for 2 hours the solution was evaporated, the residue was dissolved in 100 ml of toluene and again evaporated. The residue was taken up in 100 ml of ethyl acetate and the solution was extracted three times with 50 ml of saturated sodium bicarbonate solution. The organic phase was dried over sodium sulfate and evaporated in vacuo. The product was chromatographed on 100 g of silica gel with ether and there was obtained (4-methoxy-5-methyl-2-pyridyl)methyl acetate in the form of an oil.

(e) 47.8 g of (4-methoxy-5-methyl-2-pyridyl)methyl acetate were dissolved in 330 ml of ethanol. 165 ml of 3N sodium hydroxide solution were then added dropwise thereto at 0° and the mixture was stirred at room temperature for a further 3 hours. The ethanol was subsequently removed in vacuo, whereupon the residual aqueous solution was extracted three times with 250 ml of methylene chloride. The organic extracts were dried over sodium sulfate and evaporated in vacuo. The residue crystallizes from petroleum ether and there was obtained 4-methoxy-5-methyl-2-pyridylmethanol of melting point 101°-103°.

(f) 28.1 g of 4-methoxy-5-methyl-2-pyridylmethanol, dissolved in 180 ml of methylene chloride, were added dropwise at 0° to 17 ml of thionyl chloride in 360 ml of methylene chloride. After stirring at room temperature for 16 hours 1400 ml of ether were added dropwise thereto while cooling and the mixture was stirred at room temperature for a further 2 hours. The separated crystals were filtered off under suction and washed with ether. There was obtained 2-(chloromethyl)-4-methoxy-5-methylpyridine hydrochloride of melting point 149°-151°.

(g) 7.8 g of 5,7-dihydro-2-mercapto-5,5,7,7-tetramethylindeno[5,6-d]imidazol-6(1H)-one were suspended in 200 ml of alcohol and the suspension was treated while cooling with ice with 6.3 g of 2-chloromethyl-4- methoxy-5-methylpyridine hydrochloride. Thereafter, 2.4 g of sodium hydroxide in 100 ml of water were added dropwise thereto, the mixture was left to boil at reflux overnight and subsequently evaporated to dryness in vacuo. The residue was dissolved in 500 ml of methylene chloride. The solution was washed firstly with 250 ml of 1.5N sodium hydroxide solution and then with 3×250 ml of water, dried over sodium sulfate and evaporated in vacuo. The product was purified on 150 g of silica gel with ethyl acetate/methylene chloride (1:1) as the elution agent. Crystallization from methylene chloride/petroleum ether gave 5,7-dihydro-2-[[(4-methoxy-5-methyl-2-pyridyl)methyl]thio]-5,5,7,7-tetramethylindeno[5,6-d]imidazol-6(1H)-one of melting point 204°–205°.

EXAMPLE 19

9.5 g of 5,7-dihydro-2-[[(4-methoxy-5-methyl-2-pyridyl)methyl]thio]-5,5,7,7-tetramethylindeno[5,6-]imidazol-6(1H)-one were dissolved in 1000 ml of methylene chloride and the solution was cooled to −10° with an ice/methanol bath. 4.7 g of m-chloroperbenzoic acid, recrystallized from methylene chloride/petroleum ether, were then introduced within 30 minutes. The solution was stirred at −10° for a further 120 minutes and then poured into a mixture of 150 ml of 2N sodium carbonate solution and ice. The aqueous phase was extracted twice with 300 ml of methylene chloride. The combined organic phases were washed neutral three times with 200 ml of water, dried over sodium sulfate and concentrated at 35° in vacuo to a volume of 150 ml. Upon the addition of petroleum ether there was brought about crystallization of 5,7-dihydro-2-[[(4-methoxy-5-methyl-2-pyridyl)methyl]sulfinyl]-5,5,7,7-tetramethylindeno[5,6-d]imidazol-6(1H)-one; m.p. 191°–193°.

EXAMPLE 20

(a) 13.5 g of sodium were dissolved in 2300 ml of ethanol under argon. 60 g of 2,5-dimethyl-4-nitropyridine 1-oxide were then added portionwise thereto and the solution was left to boil under reflux overnight. The pH was adjusted to 7 with 5N hydrogen chloride in ethyl acetate while cooling, whereupon the mixture was evaporated in vacuo. The residue was taken up in 1 l of methylene chloride, the solution was filtered through silica gel, which was rinsed with 500 ml of methylene chloride, and the combined filtrates were evaporated in vacuo. The product was chromatographed on 300 g of silica gel with methylene chloride/methanol (95:5). After crystallization from ether/petroleum ether there was obtained 4-ethoxy-2,5-dimethylpyridine 1-oxide of melting point 65°–67°.

(b) 20 ml of acetic anhydride were added dropwise at room temperature to a solution of 7.8 g of 4-ethoxy-2,5-dimethylpyridine 1-oxide in 30 ml of chloroform. After boiling under reflux for 3 hours the solution was evaporated, the residue was dissolved in 50 ml of toluene and again evaporated. The residue was taken up in 50 ml of ethyl acetate, whereupon the solution was extracted three times with 20 ml of saturated sodium bicarbonate solution. The organic phase was dried over sodium sulfate and evaporated in vacuo. The product was chromatographed on 50 g of silica gel with ether and there was obtained (4-ethoxy-5-methyl-2-pyridyl)methyl acetate in the form of an oil.

(c) 7.4 g of (4-ethoxy-5-methyl-2-pyridyl)methyl acetate were dissolved in 46 ml of ethanol. 23 ml of 3N sodium hydroxide solution were then added dropwise thereto and the mixture was stirred at room temperature for a further 3 hours. The ethanol was subsequently removed in vacuo, whereupon the residual aqueous solution was extracted three times with 100 ml of methylene chloride. The organic extracts were dried over sodium sulfate and evaporated in vacuo. The residue was crystallized from petroleum ether and there was obtained 4-ethoxy-5-methyl-2-pyridylmethanol of melting point 99°–101°.

(d) 4.7 g of 4-ethoxy-5-methyl-2-pyridylmethanol, dissolved in 30 ml of methylene chloride, were added dropwise at 0° to 2.4 ml of thionyl chloride in 60 ml of methylene chloride. After stirring at room temperature for 16 hours 400 ml of ether were added dropwise thereto while cooling and the mixture was stirred at room temperature for a further 2 hours. The separated crystals were filtered off under suction and washed with ether. There was obtained 2-chloromethyl-4-ethoxy-5-methylpyridine hydrochloride of melting point 144°–146°.

(e) 6.1 g of 5,7-dihydro-2-mercapto-5,5,7,7-tetramethylindeno[5,6-d]imidazol-6(1H)-one were suspended in 100 ml of alcohol and treated while cooling with ice with 5.2 g of 2-chloromethyl-4-ethoxy-5-methylpyridine hydrochloride. Thereafter, a solution of 1.9 g of sodium hydroxide in 50 ml of water was added dropwise thereto, the mixture was left to boil at reflux overnight and subsequently evaporated to dryness in vacuo. The residue was dissolved in 300 ml of methylene chloride. The solution was washed firstly with 200 ml of 1.5N sodium hydroxide solution and then with 3×200 ml of water, dried over sodium sulfate and evaporated in vacuo. The product was purified on 120 g of silica gel with ethyl acetate/methylene chloride (1:1) as the elution agent. Crystallization from methylene chloride/petroleum ether gave 2-[[(4-ethoxy-5-methyl-2-pyridyl)methyl]thio]-5,7-dihydro-5,5,7,7-tetramethylindeno[5,6-d]imidazol-6(1H)-one of melting point 187°–189°.

EXAMPLE 21

6.1 g of 2-[[(4-ethoxy-5-methyl-2-pyridyl)methyl]thio]-5,7-dihydro-5,5,7,7-tetramethylindeno[5,6-d]imidazol-6(1H)-one were dissolved in 300 ml of methylene chloride and the solution was cooled to −30° with a dry ice/acetone bath. 4.0 g of m-chloroperbenzoic acid, recrystallized from methylene chloride/petroleum ether, were then added dropwise within 30 minutes. The solution was stirred at −10° for a further 120 minutes and then poured into a mixture of 100 ml of 2N sodium carbonate solution and ice. The aqueous phase was extracted twice with 300 ml of methylene chloride. The combined organic phases were washed neutral three times with 200 ml of water, dried over sodium sulfate and concentrated at 35° in vacuo to a volume of 120 ml. Upon the addition of petroleum ether there was brought about crystallization of 2-[[(4-ethoxy-5-methyl-2-pyridyl)methyl]sulfinyl]-5,7-dihydro-5,5,7,7-tetramethylindeno[5,6-d]imidazol-6(1H)-one, m.p. 205°–207°.

EXAMPLE 22

(a) A solution of 7.3 g of 2-chloromethyl-3-methyl-4-nitro-pyridine and 7.5 g of 5H-1,3-dioxolo[4,5-f]benzimidazole-6-thiol in 200 ml of absolute acetone was treated with 8 g of finely ground potassium carbonate, whereupon the mixture was stirred at room temperature under argon for 2 hours. The mixture was poured on to ice and the resulting crystals were filtered off, washed thoroughly with water and dissolved in acetonitrile. The solution obtained was filtered while hot. Upon cooling the filtrate there crystallized 6-[[(3-methyl-4-nitro-2-pyridyl)methyl]thio]-5H-1,3-dioxolo[4,5-f]benzimidazole of melting point 204°–205° (decomposition).

(b) A solution of 500 mg of 6-[[(3-methyl-4-nitro-2-pyridyl)methyl]thio]-5H-1,3-dioxolo[4,5-f]benzimidazole in 20 ml of absolute methanol was treated with 300 mg of sodium methylate, whereupon the mixture was boiled at reflux under argon for 18 hours. The reaction mixture was buffered by means of glacial acetic acid and concentrated in vacuo. The residue was treated with methylene chloride/sodium bicarbonate solution, whereupon the organic solution was dried and concentrated. By recrystallization from ethyl acetate there was obtained 6-[[(4-methoxy-3-methyl-2-pyridyl)methyl]thio]-5H-1,3-dioxolo[4,5-f]benzimidazole of melting point 215°–220°.

EXAMPLE 23

A solution of 330 mg of 6-[[(4-methoxy-3-methyl-2-pyridyl)methyl]thio]-5H-1,3-dioxolo[4,5-f]benzimidazole in 5 ml of chloroform was treated portionwise with 200 mg of m-chloroperbenzoic acid while cooling with ice and stirring. After 15 minutes the reaction mixture was extracted with 10% sodium carbonate solution, dried and concentrated. The residue was chromatographed on silica gel with methylene chloride/methanol (8.5:1.5) as the elution agent, the medium pressure flash chromatography method being used and the pressure being produced with nitrogen. By recrystallization from ether there was obtained 6-[[(4-methoxy-3-methyl-2-pyridyl)methyl]sulfinyl]-5H-1,3-dioxolo[4,5-f]benzimidazole of melting point 185°–186° (decomposition).

EXAMPLE 24

(a) 14.8 g of 5H-1,3-dioxolo[4,5-f]benzimidazole-6-thiol were suspended in 300 ml of alcohol and the suspension was treated while cooling with ice with 17.0 g of 2-chloromethyl-4-methoxy-3,5-dimethylpyridine hydrochloride. Thereafter, a solution of 6.0 g of sodium hydroxide in 150 ml of water was added dropwise thereto, the mixture was left to boil at reflux overnight and subsequently evaporated to dryness in vacuo. The residue was dissolved in 1000 ml of methylene chloride. The solution was washed firstly with 500 ml of 1.5N sodium hydroxide solution and then with 3×500 ml of water, dried over sodium sulfate and evaporated in vacuo. The product was purified on 300 g of silica gel using ethyl acetate/methylene chloride (1:1) as the elution agent. Crystallization from methylene chloride/petroleum ether gave 6-[[(4-methoxy-3,5-dimethyl-2-pyridyl)methyl]thio]-5H-1,3-dioxolo[4,5-f]benzimidazole of melting point 178°–179°.

(b) 1.3 g of 6-[[(4-methoxy-3,5-dimethyl-2-pyridyl)methyl]thio]-5H-1,3-dioxolo[4,5-f]benzimidazole were dissolved in 25 ml of hot methanol and the solution was treated with 40 ml of a 5N solution of hydrogen chloride in ethyl acetate. Upon the addition of ether there crystallized 6-[[(4-methoxy-3,5-dimethyl-2-pyridyl)methyl]thio]-5H-1,3-dioxolo[4,5-f]benzimidazole dihydrochloride of melting point 208°–210°.

EXAMPLE 25

13.3 g of 6-[[(4-methoxy-3,5-dimethyl-2-pyridyl)methyl]thio]-5H-1,3-dioxolo[4,5-f]benzimidazole were dissolved in 300 ml of methylene chloride and the solution was cooled to −10° with an ice/methanol bath. 7.5 g of m-chloroperbenzoic acid, recrystallized from methylene chloride/petroleum ether, were then introduced within 30 minutes. The solution was stirred at −10° for a further 120 minutes and then poured into a mixture of 300 ml of 2N sodium carbonate solution and ice. The aqueous phase was extracted twice with 300 ml of methylene chloride. The combined organic phases were washed neutral three times with 250 ml of water, dried over sodium sulfate and concentrated at 35° in vacuo to a volume of 150 ml. Upon the addition of petroleum ether there was brought about crystallization of 6-[[(4-methoxy-3,5-dimethyl-2-pyridyl)methyl]sulfinyl]-5H-1,3-dioxolo[4,5-f]benzimidazole; m.p. 192°–194°.

EXAMPLE 26

5.82 g of 5H-1,3-dioxolo[4,5-f]benzimidazole-6-thiol were suspended in 200 ml of ethanol and the suspension was treated with 7.1 g 2-chloromethyl-4-ethoxy-3,5-dimethylpyridine hydrochloride while cooling with ice. Thereafter, a solution of 2.4 g of sodium hydroxide in 100 ml of water was added dropwise thereto, the mixture was left to boil at reflux overnight and subsequently evaporated to dryness in vacuo. The residue was dissolved in 500 ml of methylene chloride. The solution was washed firstly with 250 ml of 1.5N sodium hydroxide solution and then with 3×300 ml of water, dried over sodium sulfate and evaporated in vacuo. The product was purified on 150 g of silica gel using ethyl acetate/methylene chloride (1:1) as the elution agent. Crystallization from acetonitrile gave 6-[[(4-ethoxy-3,5-dimethyl-2-pyridyl)methyl]thio]-5H-1,3-dioxolo[4,5-f]benzimidazole of melting point 184°–185°.

EXAMPLE 27

7.4 g of 6-[[(4-ethoxy-3,5-dimethyl-2-pyridyl)methyl]thio]-5H-1,3-dioxolo[4,5-f]benzimidazole were dissolved in 1000 ml of methylene chloride and the solution was cooled to −30° with dry ice/acetone. 4.3 g of m-chloroperbenzoic acid, recrystallized from methylene chloride/petroleum ether, were then introduced within 10 minutes. The solution was stirred at −30° for a further 45 minutes and then poured into a mixture of 100 ml of 2N sodium carbonate solution and ice. The aqueous phase was extracted twice with 400 ml of methylene chloride. The combined organic phases were washed neutral three times with 300 ml of water, dried over sodium sulfate and concentrated at 35° in vacuo to a volume of 100 ml. Upon the addition of petroleum ether there was brought about crystallization of 6-[[(4-ethoxy-3,5-dimethyl-2-pyridyl)methyl]sulfinyl]-5H-1,3-dioxolo[4,5-f]benzimidazole, m.p. 197°–198°.

EXAMPLE 28

5.82 g of 5H-1,3-dioxolo[4,5-f]benzimidazole-6-thiol were suspended in 200 ml of alcohol and the suspension was treated with 6.3 g of 2-chloromethyl-4-methoxy-5-methylpyridine hydrochloride while cooling. Thereafter, a solution of 2.4 g of sodium hydroxide in 100 ml of water was added dropwise thereto, the mixture was left to boil at reflux overnight and subsequently evaporated to dryness in vacuo. The residue was dissolved in 500 ml of methylene chloride. The solution was washed firstly with 250 ml of 1.5N sodium hydroxide solution and then with 3×300 ml of water, dried over sodium sulfate and evaporated in vacuo. The product was purified on 150 g of silica gel using ethyl acetate/methylene chloride (1:1) as the elution agent. Crystallization from methylene chloride/petroleum ether gave 6-[[(4-methoxy-5-methyl-2-pyridyl)-methyl]thio]-5H-1,3-dioxolo[4,5-f]benzimidazole of melting pont 191°–193°.

EXAMPLE 29

4.3 g of 6-[[(4-methoxy-5-methyl-2-pyridyl)methyl]-thio]-5H-1,3-dioxolo[4,5-f]benzimidazole were dissolved in 100 ml of methylene chloride and the solution was cooled to −10° with an ice/methanol bath. 3.0 g of m-chloroperbenzoic acid, recrystallized from methylene chloride/petroleum ether, were then introduced within 30 minutes. The solution was stirred at −10° for a further 120 minutes and then poured into a mixture of 100 ml of 2N sodium carbonate solution and ice. The aqueous phase was extracted twice with 100 ml of methylene chloride. The combined organic phases were washed neutral three times with 150 ml of water, dried over sodium sulfate and concentrated at 35° in vacuo to a volume of 50 ml. Upon the addition of petroleum ether there was brought about crystallization of 6-[[(4-methoxy-5-methyl-2-pyridyl)-methyl]sulfinyl]-5H-1,3-dioxolo[4,5-f]benzimidazole; m.p. 182°–184°.

EXAMPLE 30

(a) A solution of 500 mg of 5,7-dihydro-2-mercapto-5,5,7,7-tetramethylindeno[5,6-d]imidazol-6(1H)-one in 50 ml of 1,2-dichloroethane can be treated with 790 mg of phosphorus trichloride and the mixture can be heated under reflux for 16 hours. After cooling the mixture can be poured on to ice and sodium carbonate. The resulting mixture can be extracted with methylene chloride, the organic phase can be dried and the solvent can be removed on a rotary evaporator. The 5,7-dihydro-2-chloro-5,5,7,7-tetramethylindeno[5,6-d]imidazol-6(1H)-one remaining as the residue can be processed as the product.

(b) A solution of 470 mg of 2-chloromethyl-3-methyl-4-methoxypyridine dissolved in 50 ml of methylene chloride can be treated with 5 ml of triethylamine and 0.8 ml of thioacetic acid and the mixture can be stirred at room temperature overnight. The solution can be poured on to ice and sodium carbonate. The mixture can be extracted with methylene chloride, the organic phase can be dried and the solvent can be removed. The 2-acetylthiomethyl-3-methyl-4-methoxypyridine remaining as the residue can be processed as is in the next step.

(c) A solution of 500 mg of the above 2-acetylthiomethyl-3-methyl-4-methoxypyridine in 20 ml of methanol can be treated with 5 ml of triethylamine and the mixture can be stirred overnight at room temperature under nitrogen. After removing the solvent on a rotary evaporator there will remain as the residue 2-thiomethyl-3-methyl-4-methoxypyridine which can be processed directly, in the next step.

(d) A solution of 500 mg of the 5,7-dihydro-2-chloro-5,5,7,7-tetramethylindeno[5,6-d]imidazol-6(1H)-one obtained in accordance with (a) and 330 mg of the 2-thiomethyl-3-methyl-4-methoxypyridine obtained in accordance with (c) in 50 ml of acetone can be treated with 2.5 g of finely powdered potassium carbonate and the mixture can be stirred under argon for 18 hours at room temperature. After filtration and removal of the solvent the residue can be chromatographed on silica gel with methylene chloride/ethyl acetate (10:1, medium pressure flash chromatography). By recrystallization from ethyl acetate/ether there can be obtained 5,7-dihydro-2-[[(4-methoxy-3-methyl-2-pyridyl)methyl]thio]-5,5,7,7-tetramethylindeno[5,6-d]imidazol-6(1H)-one of melting point 218°–220°.

EXAMPLE A

Compounds of formula I can be used as active substances in hard gelatine capsules, the content of which have the following composition per capsule:

| | |
|---|---|
| Active substance | 50.0 mg |
| Lactose powder | 40.0 mg |
| Lactose crystals | 130.0 mg |
| Maize starch white | 20.0 mg |
| Talc | 8.0 mg |
| Magnesium stearate | 2.0 mg |
| Fill weight per capsule | 250.0 mg |

The active substance and the adjuvants are mixed with one another and the mixture can be filled into hard gelatine capsules of suitable size. If required, the capsules are subsequently provided with a gastric juice-resistant coating consisting of hydroxypropylmethylcellulose phthalate.

We claim:

1. A compound of the formula

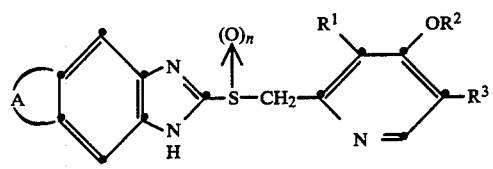

wherein one of $R^1$ and $R^3$ is lower alkyl and the other is hydrogen or lower alkyl, $R^2$ is lower alkyl, n is the number 0 or 1, A is

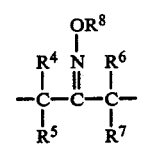

wherein $R^4$, $R^5$, $R^6$ and $R^7$ each is lower alkyl and $R^8$ is hydrogen or lower alkyl; or a pharmaceutically acceptable acid addition salt thereof.

2. A compound in accordance with claim 1, wherein A is

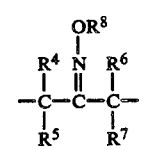

wherein $R^4$, $R^5$, $R^6$ and $R^7$ each is lower alkyl and $R^8$ is hydrogen or lower alkyl.

3. A compound in accordance with claim 2, wherein A is

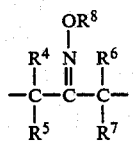

wherein $R^4$, $R^5$, $R^6$ and $R^7$ each is methyl and $R^8$ is hydrogen or methyl.

4. A compound in accordance with claim 1, wherein $R^2$ is methyl or ethyl.

5. A compound in accordance with claim 1, wherein $R^1$ is hydrogen and $R^3$ is methyl.

6. A compound in accordance with claim 1, wherein $R^1$ is methyl and $R^3$ is hydrogen.

7. A compound in accordance with claim 1, wherein $R^1$ and $R^3$ each is methyl.

8. A compound in accordance with claim 1, 5,7-Dihydro-2-[[(4-methoxy-3-methyl-2-pyridyl)-methyl]thio]-5,5,7,7-tetramethylindeno[5,6-d]imidazol-6(1H)-one O-methyl oxime.

9. A compound in accordance with claim 1, 5,7-Dihydro-2-[[(4-methoxy-3-methyl-2-pyridyl)-methyl]sulfinyl]-5,5,7,7-tetramethylindeno[5,6-d]imidazol-6(1H)-one O-methyl oxime.

10. A compound in accordance with claim 4 wherein $R^1$ is hydrogen and $R^3$ is methyl.

11. A compound in accordance with claim 4 wherein $R^1$ and $R^3$ each is methyl.

12. A compound in accordance with claim 4, wherein n is 0.

13. A compound in accordance with claim 12 wherein $R^1$ is methyl and $R^3$ is hydrogen.

14. A pharmaceutical composition for the control or prevention of ulcers and/or the control or prevention of increased gastric acid secretion comprising an effective amount of a compound of the formula

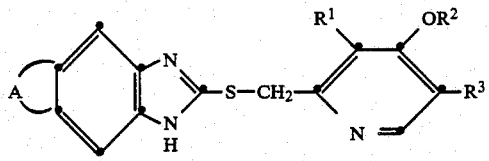

wherein one of $R^1$ and $R^3$ is lower alkyl and the other is hydrogen or lower alkyl, $R^2$ is lower alkyl, A is

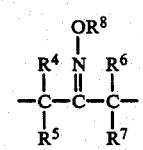

wherein $R^4$, $R^5$, $R^6$ and $R^7$ each is lower alkyl, and $R^8$ is hydrogen or lower alkyl; or a pharmaceutically acceptable acid addition salt thereof; and one or more therapeutically inert excipients.

15. A pharmaceutical composition for the control or prevention of ulcers and/or the control or prevention of increased gastric acid secretion comprising an effective amount of a compound of the formula

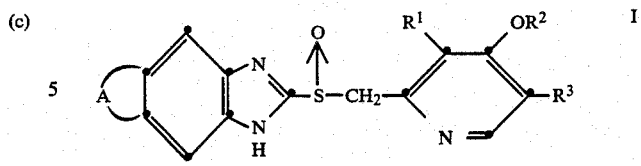

wherein one of $R^1$ and $R^3$ is lower alkyl and the other is hydrogen or lower alkyl, $R^2$ is lower alkyl, A is

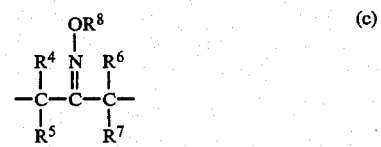

wherein $R^4$, $R^5$, $R^6$ and $R^7$ each is lower alkyl, and $R^8$ is hydrogen or lower alkyl; or a pharmaceutically acceptable acid addition salt thereof; and one or more therapeutically inert excipients and when in a form for oral administration, said composition is resistant to gastric juice.

16. A pharmaceutical composition in accordance with claim 15, which is for oral administration, and which is resistant to gastric juice.

17. A composition in accordance with claim 14, wherein $R^1$ is methyl and $R^3$ is hydrogen.

18. A composition in accordance with claim 17, wherein the compound of formula I is, 5,7-dihydro-2-[[(4-methoxy-3-methyl-2-pyridyl)-methyl]thio]5,5,7,7-tetramethylindeno[5,6-d]imidazol-6(1H)-one O-methyl oxime.

19. A composition in accordance with claim 15, wherein $R^1$ is methyl and $R^3$ is hydrogen.

20. A composition in accordance with claim 19, wherein the compound of formula I is, 5,7-dihydro-2-[[(4-methoxy-3-methyl-2-pyridyl)methyl]sulfinyl]-5,5,7,7-tetramethylindeno[5,6-d]imidazol-6(1H)-one O methyl oxime.

21. A method of controlling or preventing ulcers which comprises administering a composition containing an antiulcerogenically effective amount of a compound of the formula

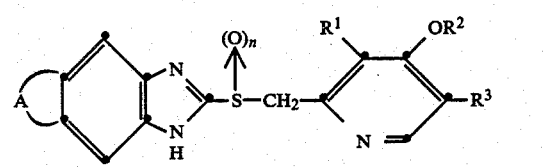

wherein one of $R^1$ and $R^3$ is lower alkyl and the other is hydrogen or lower alkyl, $R^2$ is lower alkyl, n is the number 0 or 1, A is

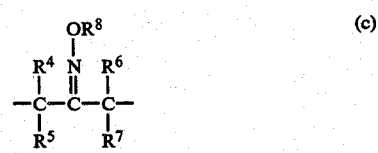

wherein $R^4$, $R^5$, $R^6$ and $R^7$ each is lower alkyl, and $R^8$ is hydrogen or lower alkyl; or a pharmaceutically acceptable acid addition salt thereof and when n is 1 and said composition is administered orally, said composition is resistant to gastric juice.

22. A method in accordance with claim 21 wherein when n is 1, the composition is administered orally in a form resistant to gastric juice.

23. A method in accordance with claim 21 wherein n is 0.

24. A method of controlling or preventing increased gastric acid secretion which comprises administering an amount, effective for controlling or preventing increased gastric acid secretion, of a composition containing a compound of the formula

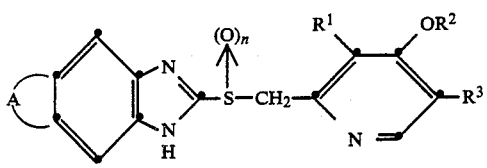

wherein one of $R^1$ and $R^3$ is lower alkyl and the other is hydrogen or lower alkyl, $R^2$ is lower alkyl, n is the number 0 or 1, A is

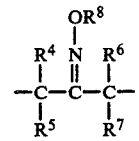

(c)

wherein $R^4$, $R^5$, $R^6$ and $R^7$ each is lower alkyl, and $R^8$ is hydrogen or lower alkyl; or a pharmaceutically acceptable acid addition salt thereof and when n is 1 and said composition is administered orally, said composition is resistant to gastric juice.

25. A method in accordance with claim 24 wherein when n is 1, the composition is administered orally in a form resistant to gastric juice.

26. A method in accordance with claim 24 wherein n is 0.

27. A method in accordance with claim 21, wherein $R^1$ is methyl and $R^3$ is hydrogen.

28. A method in accordance with claim 27, wherein the compound of formula I is 5,7-dihydro-2-[[(4-methoxy-3-methyl-2-pyridyl)-methyl]thio-]5,5,7,7-tetramethylindeno[5,6-d]imidazol-6(1H)-one O methyl oxime.

29. A method in accordance with claim 24, wherein $R^1$ is methyl and $R^3$ is hydrogen.

30. A method in accordance with claim 27, wherein the compound of formula I is 5,7-dihydro-2-[[(4-methoxy-3-methyl-2-pyridyl)-methyl]sulfinyl-]5,5,7,7-tetramethylindeno[5,6-d]imidazol-6(1H)-one O methyl oxime.

* * * * *